United States Patent [19]

Utton et al.

[11] 4,431,315
[45] Feb. 14, 1984

[54] DETERMINATION OF HEAT TRANSFER FROM A SURFACE

[75] Inventors: Donald B. Utton; Mark A. Sheppard, both of Leicestershire, England

[73] Assignee: National Nuclear Corporation Limited, London, England

[21] Appl. No.: 382,427

[22] Filed: May 27, 1982

[30] Foreign Application Priority Data

Jun. 3, 1981 [GB] United Kingdom ............... 8117043

[51] Int. Cl.³ ............................................. G01K 17/00
[52] U.S. Cl. .......................................... 374/29; 374/54
[58] Field of Search .................... 374/29, 43, 54, 17, 374/18, 19, 45; 356/43, 436, 445, 432; 250/573; 73/73, 75, 336.5

[56] References Cited

U.S. PATENT DOCUMENTS 3,150,264  9/1964  Ehlert ..................................... 73/73
3,538,770  11/1970 Hawley ............................... 73/336.5
4,083,224  4/1978  Gayst ................................... 374/19

Primary Examiner—Charles E. Frankfort
Assistant Examiner—David R. Schuster
Attorney, Agent, or Firm—Kirschstein, Kirschstein, Ottinger & Israel

[57] ABSTRACT

A method of determining the rate of heat transfer from a surface due to fluid convection, in which a sheet of liquid absorbent material, whose transmissive or reflective properties for certain radiations vary with the liquid content, is attached to the surface and, after being wetted with a liquid which will evaporate on passage of the convective fluid, the sheet is exposed to the radiation and to the convecting fluid, and the change in the amount of radiation transmitted through or reflected from the sheet is monitored, this giving a ready indication of the rate of heat transfer.

9 Claims, 3 Drawing Figures

DETERMINATION OF HEAT TRANSFER FROM A SURFACE

This invention relates to a method of determining the rate of heat transfer from a surface due to fluid convection, and to apparatus for carrying out said method.

Existing methods of determining the rates of heat transfer from surfaces as a result of fluid convection commonly involve a considerable number of temperature measurements and complex calculations, and an object of the present invention is to provide an alternative method which has the advantage of requiring less complex equipment and results in a significant saving in terms of costs and time compared with the usually expensive direct measurements of heat transfer rates as carried out hitherto.

According therefore to one aspect of the invention a method of determining the rate of heat transfer from a surface due to fluid convection, comprises attaching to said surface a sheet of liquid absorbent material, whose transmissive or reflective properties for certain radiations vary with the liquid content of the material, wetting the sheet of material with a liquid which will evaporate on passage of the convecting fluid, exposing the sheet to said radiation and to the convecting fluid, and detecting the change in the amount of radiation transmitted through or reflected from the sheet.

Thus it has been found that the rate of heat transfer is a function of the mass transfer rate, e.g. the evaporation rate, and the variation in the transmission or reflection of said radiation in a given time gives a ready indication of the rate of heat transfer.

Preferably the sheet material used has a transmission or reflection coefficient which is proportional to its liquid content, and it may, for example, be formed of paper.

The convecting fluid is preferably one which does not contain the substance used to wet the paper. Accordingly where atmospheric air is the convecting fluid, use of a non-aqueous liquid, for example alcohol is preferably used as the liquid wetting agent.

Visible light is conveniently the radiation employed, the light source being arranged to illuminate the sheet directly, or alternatively indirectly by means of an optical fibre or other suitable device. Similarly the light detector can either be positioned to receive the transmitted or reflected light directly, or be arranged to sense the light remotely by the use of an optical fibre or other device.

However if the coefficient of transmission and/or reflection of the sheet with respect to radiations of other wavelengths varies with the liquid content of the sheet such radiations could alternatively be employed in place of visible light.

The invention includes within its scope apparatus for carrying out the method above described.

According, therefore, to another aspect of the invention, apparatus for use in determining the rate of heat transfer from a surface as a result of fluid convection, comprises a sheet of liquid absorbent material, such as paper, whose transmissive or reflective properties for certain radiations vary with the liquid content of the material, for attachment to said surface, a source of said radiation arranged to direct radiation on to said surface, either directly or indirectly, a detector for receiving radiation transmitted through or reflected from the sheet of material when attached to said surface, and means for recording the change and rate of change of the transmitted or reflected radiation.

Different ways of determining heat transfer rates from a surface in accordance with the invention, and equipment for achieving this, will now be described by way of example with reference to FIGS. 1 to 3 of the accompanying drawings.

BRIEF DESCRIPTION OF THE DRAWINGS

Referring to FIG. 1, this shows a light source 1 such as a tungsten filament incandescent lamp and a detector 2, such as a photo transistor responsive to light issuing from the source. The output from the detector 2 being fed to a rate of change detector 3 which, in turn, feeds a recorder 4 of any convenient kind. The output from the detector 3 is also fed directly to the recorder 4.

Figure 1:
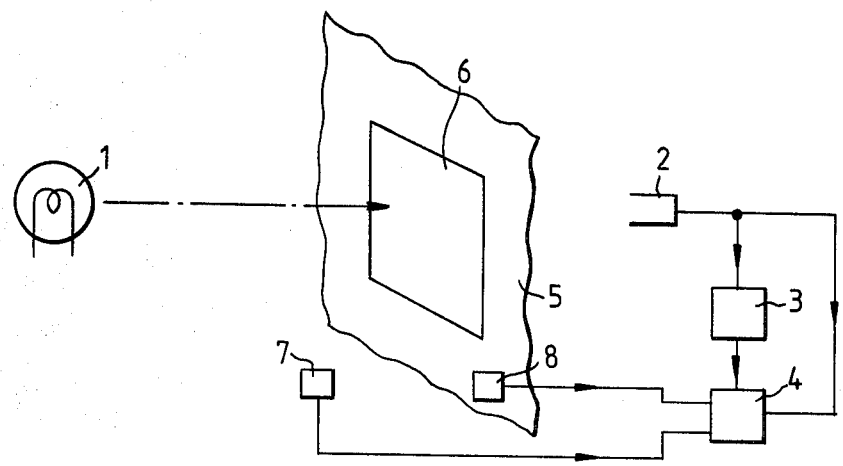
FIG. 1 is a light transmitting embodiment of the invention.

To the surface 5 under investigation, in this case a transparent surface, there is attached a sheet 6 of liquid absorbent paper having a coefficient of light transmission which is proportional to its liquid content, one such paper being typical blotting paper. In use the detector is positioned to receive light from the light source 1 which is transmitted through the sheet 6.

The sheet is wetted with a liquid, and is exposed to the convecting fluid which may, for example, be air although it could be another gas or in some cases a different liquid.

Means of any suitable kind, such as thermocouples indicated diagrammatically at 7 and 8, are provided for measuring the temperature of the fluid and of the surface 5, the output being also fed to the recorder 4, or possibly to a separate recorder as may be convenient.

The change in the amount of light transmitted through the paper, together with the rate of change, give an indication of the rate of evaporation of the liquid from the paper 6 from which the rate of heat transfer may readily deduced. A correction also needs to be applied to the observed evaporation rate if the convecting fluid contains any substance used to wet the paper; accordingly a non-aqueous liquid, e.g. alcohol, is particularly useful when atmospheric air is used as the convecting fluid. If desired the light detector 2 can be arranged to sense the light remotely by the use of a telescope or a fibre optic device. Similarly the light source 1 may indirectly illuminate the paper 6 by means of a fibre optic or other device.

Where the surface under investigation is not transparent the detector 2 can be arranged to receive reflected instead of transmitted light, the paper being such that its coefficient of reflection varies with its liquid content; a suitable paper in this case is also typical blotting paper. Equipment for determining the rate of heat transfer from the surface 5 in such a case is illustrated in FIG. 2, the equipment being otherwise similar to that shown in FIG. 1, the same parts being denoted by the same reference numerals.

Measurement of the rate of heat transfer is effected in the same way as with the equipment previously described, the detector 2 being either positioned to receive the reflected light directly or alternatively indirectly by means of an optical fibre or other suitable device.

Figure 2:
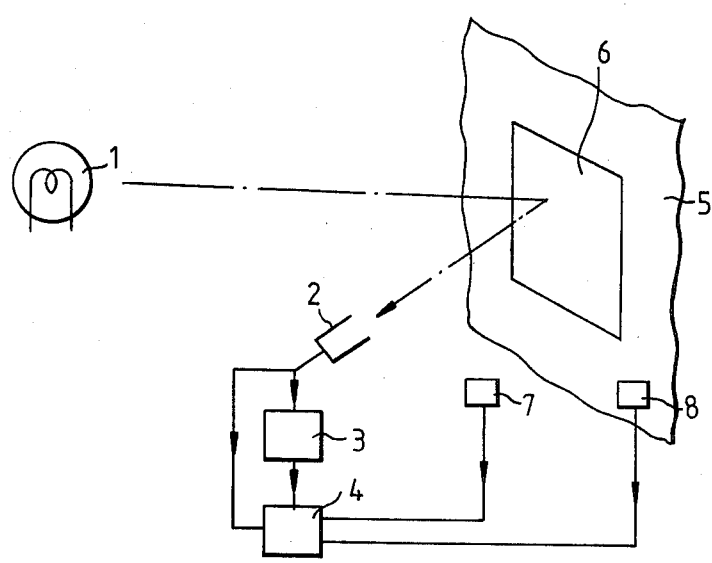
FIG. 2 is a light reflective embodiment of the invention.
Figure 3:
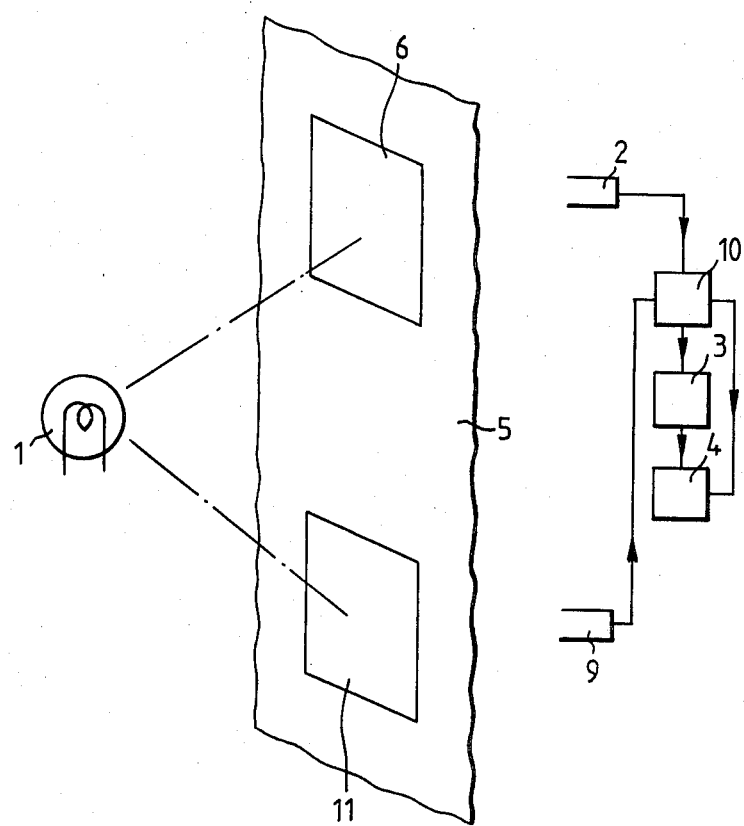
FIG. 3 is a modified embodiment of FIG. 1 wherein a reference sheet is contained.

A modification of the equipment illustrated in FIG. 1 is shown in FIG. 3. In this arrangement there is provided a second detector 9 arranged to receive light from the light source 1 which is transmitted through an identical but dry (or whose light transmitting properties do not change during the course of the measurements) reference sheet 11 of paper attached to the surface 5. The outputs from the two detectors 2, 9 are fed to a difference amplifier 10 which feeds a difference signal to the rate detector 3 and also to the recorder 4.

This difference technique has the advantage of reducing the effect of unwanted variations in the light source intensity and variations in the detector sensitivity and hence reduces the scatter of the measurements.

A similar modification of the arrangement illustrated in FIG. 2 may also be employed if desired.

We claim:

1. A method of determining the rate of heat transfer from a surface due to convection of a fluid, comprising attaching to said surface a sheet of liquid absorbent material, whose transmissive or reflective properties for certain radiations vary with the liquid content of the material, wetting the sheet of material with a liquid which will evaporate on passage of the convecting fluid adjacent said surface, exposing the sheet to said radiation and to the convecting fluid, and detecting the change in the amount of radiation transmitted through or reflected from the sheet to determine the rate of heat transfer from said surface.

2. A method according to claim 1 wherein the sheet material has a transmission or reflection coefficient which is proportional to its liquid content.

3. A method according to claim 2 wherein the sheet material is formed of a liquid absorbent paper.

4. A method according to claim 1 in which air is the convecting fluid and the sheet material is wetted by a non-aqueous liquid.

5. A method according to claim 4 in which the non-aqueous liquid is alcohol.

6. A method according to claim 1 in which the said radiations are provided by visible light.

7. A method of determining the rate of heat transfer from a surface due to convection of a fluid comprising attaching to said surface two sheets of liquid absorbent material, whose transmissive or reflective properties for certain radiations vary with the liquid content of the material, wetting one sheet of material with a liquid which will evaporate on passage of the convecting fluid adjacent said surface, exposing both sheets to said radiation and to the convecting fluid, detecting the difference in the amount of radiation transmitted through or reflected from the two sheets, and recording the change and rate of change of said difference to determine the rate of heat transfer from said surface.

8. Apparatus for use in determining the rate of heat transfer from a surface as a result of convection of a fluid, comprising a sheet of liquid absorbent material whose transmissive or reflective properties for certain radiations vary with the liquid content of the material, said sheet of liquid absorbant material being attached to said surface, a source of said radiation arranged to direct radiation on to said surface and said sheet of material, either directly or indirectly, a detector for receiving radiation transmitted through or reflected from the sheet of material when attached to said surface to determine the rate of heat tansfer from said surface, and means for recording the change and rate of change of the transmitted or reflected radiation.

9. Apparatus for use in determining the rate of heat transfer from a surface as a result of convection of a fluid, comprising two substantially identical sheets of liquid absorbent material whose transmissive or reflective properites for certain radiations vary with the liquid content of the material said sheets of material being attached to said surface, a source of radiation arranged to direct radiation on to said surface and said sheets of material, either directly or indirectly, two detectors for receiving radiation transmitted through or reflected from a respective one of the sheets of material to determine the rate of heat transfer from said surface, a difference amplifier responsive to the outputs of the two detectors for producing a signal, and means for recording the change and rate of change of the difference signal.

* * * * *